United States Patent
Klein

(10) Patent No.: US 10,014,475 B2
(45) Date of Patent: Jul. 3, 2018

(54) GRAPHENE NANORIBBONS AS SEMICONDUCTORS FOR ORGANIC THIN FILM TRANSISTORS

(71) Applicant: EMPIRE TECHNOLOGY DEVELOPMENT LLC, Wilmington, DE (US)

(72) Inventor: Josef Peter Klein, Vashon, WA (US)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 30 days.

(21) Appl. No.: 14/785,323

(22) PCT Filed: Apr. 17, 2013

(86) PCT No.: PCT/US2013/036906
§ 371 (c)(1),
(2) Date: Oct. 17, 2015

(87) PCT Pub. No.: WO2014/171931
PCT Pub. Date: Oct. 23, 2014

(65) Prior Publication Data
US 2016/0087212 A1 Mar. 24, 2016

(51) Int. Cl.
| | |
|---|---|
| C01B 31/02 | (2006.01) |
| H01L 51/00 | (2006.01) |
| H01L 21/02 | (2006.01) |
| C07C 1/26 | (2006.01) |
| C07C 2/76 | (2006.01) |
| C07C 5/48 | (2006.01) |
| C07C 15/20 | (2006.01) |
| C07C 17/281 | (2006.01) |
| C07C 17/361 | (2006.01) |
| C01B 32/184 | (2017.01) |
| H01L 29/06 | (2006.01) |
| H01L 51/05 | (2006.01) |

(52) U.S. Cl.
CPC ........ *H01L 51/0045* (2013.01); *C01B 32/184* (2017.08); *C07C 1/26* (2013.01); *C07C 2/76* (2013.01); *C07C 5/48* (2013.01); *C07C 15/20* (2013.01); *C07C 17/281* (2013.01); *C07C 17/361* (2013.01); *H01L 21/0262* (2013.01); *H01L 21/02527* (2013.01); *H01L 51/0056* (2013.01); *C01B 2204/06* (2013.01); *C01B 2204/065* (2013.01); *H01L 29/0673* (2013.01); *H01L 51/0545* (2013.01); *H01L 51/0558* (2013.01)

(58) Field of Classification Search
CPC ............ H01L 51/0045; H01L 21/0262; H01L 51/0056; H01L 21/02527; H01L 51/0558; H01L 51/0545; H01L 29/0673; C07C 17/361; C07C 1/26; C07C 2/76; C07C 5/48; C07C 17/281; C07C 15/20; C01B 31/0446; C01B 2204/065; C01B 2204/06
See application file for complete search history.

(56) References Cited

U.S. PATENT DOCUMENTS

| | | |
|---|---|---|
| 5,872,369 A | 2/1999 | Inokuchi |
| 6,528,605 B1 | 3/2003 | Akiike et al. |
| 6,852,370 B2 | 2/2005 | Shinohara et al. |
| 2007/0155997 A1 | 7/2007 | Li et al. |
| 2010/0120984 A1 | 5/2010 | Ozawa et al. |
| 2011/0042649 A1 | 2/2011 | Duvall et al. |
| 2011/0220883 A1 | 9/2011 | Nakano et al. |
| 2012/0261644 A1 | 10/2012 | Dimitrakopoulos |

FOREIGN PATENT DOCUMENTS

WO 2012149257 A2 11/2012

OTHER PUBLICATIONS

Fogel, Yulia, et al. "Graphitic nanoribbons with dibenzo [e, 1] pyrene repeat units: synthesis and self-assembly." Macromolecules 42.18 (2009): 6878-6884.*

Jinming Cai et al., "Atomically Precise Bottom-up Fabrication of Graphene Nanoribbons", Nature, Jul. 22, 2010, pp. 470-473.

Tse-An Chen et al., "Regiocontrolled Synthesis of Ethene-Bridged para-Phenylene Oligomers Based on Pt(II)- and Ru(II)-Catalyzed Aromatization", Chemistry—A European Journal, 2010, pp. 1826-1833, vol. 16.

Vincent Diemer et al., "Efficient and Complementary Methods Offering Access to Synthetically Valuable 1, 2-Dibromobenzenes", European Journal of Organic Chemistry, 2011, pp. 327-340.

International Search Report and Written Opinion of the International Searching Authority, International application No. PCT/US2013/036906, dated Nov. 5, 2013.

Jin Jang, "Displays Develop a New Flexibility", Materialstoday, Apr. 2006, pp. 46-52, vol. 9, No. 4.

Xiaoting Jia et al., "Controlled Formation of Sharp Zigzag and Armchair Edges in Graphitic Nanoribbons", Science, Mar. 27, 2009, pp. 1701-1705, vol. 323.

Xiaolin Li et al., "Chemically Derived, Ultrasmooth Graphene Nanoribbon Semiconductors", Science, Feb. 29, 2008, pp. 1229-1232, vol. 319.

Amanda R. Murphy et al., "Organic Semiconducting Oligomers for Use in Thin Film Transistors", Chemical Reviews, 2007, pp. 1066-1096.

B. Obradovic et al., "Analysis of Graphene Nanoribbons as a Channel Material for Field-Effect Transistors", Applied Physics Letters, 2006, pp. 142012-142012-3, vol. 88.

Upendra Kumar Parashar et al., "Single Step Synthesis of Graphene Nanoribbons by Catalyst Particle Size Dependent Cutting of Multiwalled Carbon Nanotubes", Nanoscale, 2011, pp. 3876-3882, vol. 3.

Adam Pron et al., "Cheminform Abstract: Electroactive Materials for Organic Electronics: Preparation Strategies, Structural Aspects and Characterization Techniques", Chemical Society Reviews, 2010, pp. 2577-2632, vol. 39.

(Continued)

*Primary Examiner* — Richard M Rump

(57) ABSTRACT

Disclosed herein are graphene nanoribbons, controllable and reproducible methods of synthesizing graphene nanoribbons, and uses thereof. Transistors containing graphene nanoribbons are also disclosed.

24 Claims, No Drawings

(56) References Cited

OTHER PUBLICATIONS

Frank Schwierz, "Graphene Transistors", Nature Nanotechnology, Jul. 2010, pp. 487-496, vol. 5.
Alexandr V Talyzin et al., "Synthesis of Graphene Nanoribbons Encapsulated in Single-Walled Carbon Nanotubes", Nano Letters, pp. 4352-4356.
Mauricio Terrones, "Sharpening the Chemical Scissors to Unzip Carbon Nanotubes: Crystalline Graphene Nanoribbons", ACSNANO, 2010, pp. 1775-1781, vol. 4, No. 4.
Chengliang Wang et al., "Semiconducting $\pi$-Conjugated Systems in Field-Effect Transistors: A Material Odyssey of Organic Electronics", Chemical Reviews, 2012, pp. 2208-2267, vol. 112.
Xinran Wang et al., "Room Temperature All Semiconducting Sub-10nm Graphene Nanoribbon Field-Effect Transistors", Physical Review Letters, May 23, 2008, vol. 100.
Yugeng Wen et al., "Experimental Techniques for the Fabrication and Characterization of Organic Thin Films for Field-Effect Transistors", Chemical Reviews, 2011, pp. 3358-3406, vol. 111.
Xiaoyin Yang et al., "Two-Dimensional Graphene Nanoribbons", Journal of the American Chemical Society, 2008, pp. 4216-4217, vol. 130.
Felix Plasser et al., "The Multiradical Character of One- and Two-Dimensional Graphene Nanoriboons", Angewandte Chem. Int. Ed., 2013, pp. 2581-2584, vol. 52.

\* cited by examiner

GRAPHENE NANORIBBONS AS SEMICONDUCTORS FOR ORGANIC THIN FILM TRANSISTORS

CROSS-REFERENCE TO RELATED APPLICATION

The present application is a U.S. National Stage filing under 35 U.S.C. § 371 of International Application No. PCT/US2013/036906, filed on Apr. 17, 2013 and entitled "GRAPHENE NANORIBBONS AS SEMICONDUCTORS FOR ORGANIC THIN FILM TRANSISTORS." The International Application, including any appendices or attachments thereof, is incorporated herein by reference in its entirety.

BACKGROUND

Graphene nanoribbons represent promising semiconductor materials. Graphene nanoribbons are typically synthesized by "cutting" or "unzipping" carbon nanotubes resulting in irregularities such as irregular and undefined edge structures. There is a need for alternative approaches for the reproducible and controlled chemical synthesis of graphene nanoribbons. Organic thin film transistors (OTFTs) incorporating semiconductors are widely utilized as electronic components in flexible displays. There is also a need for synthetically feasible alternatives to small molecule and polymeric semiconductors for applications including but not limited to OTFTs and graphene nanoribbon field effect transistors (FETs) for application in non-flexible electronics and materials reinforcement.

SUMMARY

Embodiments described herein are directed to methods for synthesizing a graphene nanoribbon, the method comprising: providing a linearly conjugated aryl compound having a formula (I):

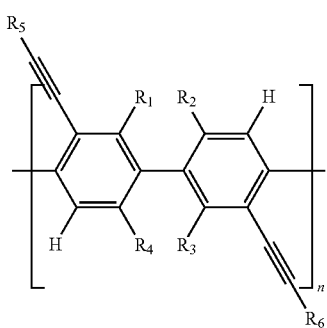

(I)

wherein n is an integer of 1 to 100,000; $R_1$ to $R_4$ are independently selected from H and

$R_7$;

$R_5$ to $R_7$ are independently selected from H, alkyl, aryl, and trimethylsilyl; and polycyclization of the linearly conjugated aryl compound to provide a graphene nanoribbon precursor.

Some embodiments are directed to methods of synthesizing a graphene nanoribbon having a zigzag backbone; the method comprising providing a zigzag conjugated aryl compound having a formula (VI):

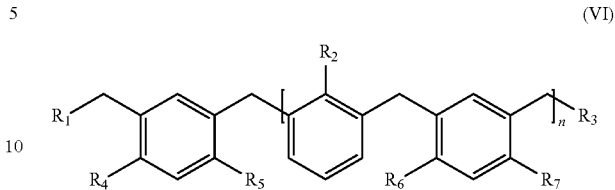

(VI)

wherein $R_1$ and $R_3$ are independently selected from hydrogen, fluorine, chlorine, bromine, iodine, lithium, astantine, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide; wherein $R_2$ is independently selected from a hydrogen, trimethylsilyl, tert-butyldimethylsilyl, tert-butyldiphenylsilyl, triethylsilyl, triisopropylsilyl, alkyl, phenyl, furanyl, thiophenyl, pyridyl, or poly (m-phenylene) comprising about 2 to about 20 m-phenylene units; wherein $R_4$ to $R_7$ are independently selected from an aldehyde group and an acetal group; and polcyclizing the zigzag conjugated aryl compound to provide a graphene nanoribbon precursor.

Some embodiments are directed to a compound having the structure of the following formula (XII):

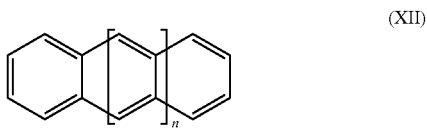

(XII)

wherein n is an integer of about 5 to about 100,000. Some embodiments are directed to a transistor comprising the compound of formula XII.

Some embodiments are directed to a compound having a structure of the following formula (XIII):

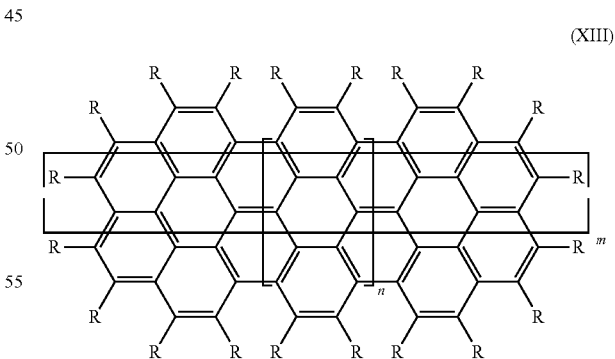

(XIII)

wherein n is an integer of about 5 to about 100,000, m is an integer of 0 to 20, and wherein each R is independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms and wherein the alkyl groups may be combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms, or a cyano group. Some embodiments are directed to a transistor comprising the compound of formula XIII.

Some embodiments are directed to an organic thin film transistor comprising: a substrate; and a gate electrode, a source electrode and a drain electrode, an insulator layer and an organic semiconductor layer being provided on the substrate; a source-drain cover controllable by applying a voltage to the gate electrode whereby the organic thin film transistor performs and on-off operation; and wherein the semiconductor layer comprises a compound of formula (XIV):

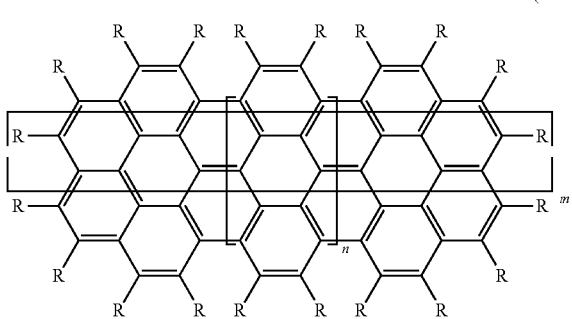

(XIV)

wherein n is an integer of about 5 to about 100,000, m is an integer of 0 to 20, and wherein each R is independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms and wherein the alkyl groups may be combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms, or a cyano group. Some embodiments are directed to an apparatus comprising the organic thin film transistor of formula XIV.

Some embodiments are directed to an organic thin film transistor comprising: a substrate; and a gate electrode, a source electrode and a drain electrode, an insulator layer and an organic semiconductor layer being provided on the substrate; a source-drain cover controllable by applying a voltage to the gate electrode whereby the organic thin film transistor performs and on-off operation; and wherein the semiconductor layer comprises a compound of formula (XV):

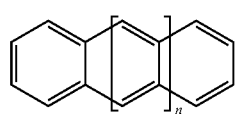

(XV)

wherein n is an integer of 0 to about 100,000. Some embodiments are directed to an apparatus comprising the organic thin film transistor of formula XV.

DETAILED DESCRIPTION

Embodiments described herein include methods for synthesizing graphene nanoribbons. The graphene nanoribbons produced by the methods described herein can have multiple applications including, but not limited to, their use as semiconductors for organic thin film transistors (OTFTs) ultra-light weight materials reinforcement. In the various methods, components may be added in a single batch, in multiple portions, or continuously.

Methods for Synthesizing a Graphene Nanoribbon

Some embodiments are a method for synthesizing a graphene nanoribbon. The method can include providing a linearly conjugated aryl compound having a formula (I):

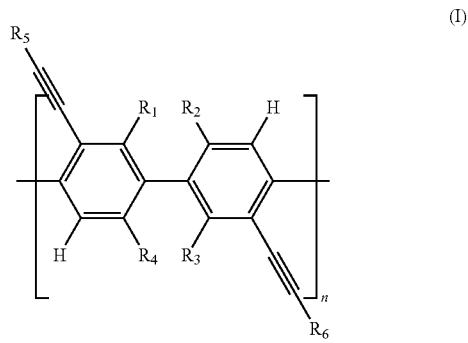

(I)

wherein n is an integer of 1 to 100,000; $R_1$ to $R_4$ are independently selected from H and

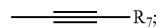

$R_5$ to $R_7$ are independently selected from H, alkyl, aryl, and trimethylsilyl; and polycyclization of the linearly conjugated aryl compound to provide a graphene nanoribbon precursor.

Some embodiments include coupling a first aryl monomer and a second aryl monomer to provide a linearly conjugated aryl compound intermediate. In some embodiments, the first aryl monomer has a formula (II):

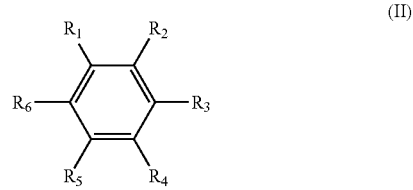

(II)

wherein $R_1$ to $R_6$ are independently selected from hydrogen, fluorine, chlorine, bromine, iodine, lithium, astatine, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide; and wherein the second aryl monomer has a formula (III):

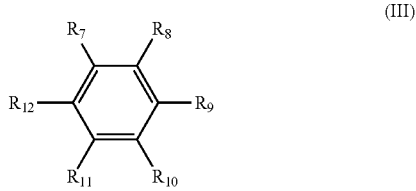

wherein $R_7$ to $R_{12}$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide.

In some embodiments, the first aryl monomer has a formula (V):

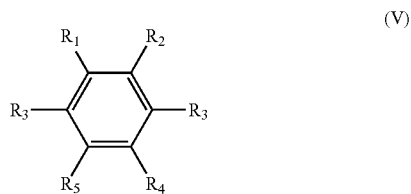

wherein $R_1$ to $R_5$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide; and wherein the second aryl monomer has a formula (VI):

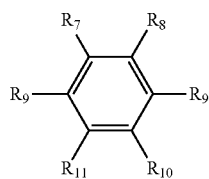

wherein $R_7$ to $R_{11}$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide.

In some embodiments, the first aryl monomer is a dihalophenyl diboronate compound and the second aryl monomer is a dihalodiodobenzene compound. In some embodiments, the dihalophenyl diboronate compound is 2,3,dibromophenyl-1,4-diboronate, 2,5,dibromophenyl-1,4-diboronate, 2,3,dichlorophenyl-1,4-diboronate, and 2,5,dichlorophenyl-1,4-diboronate. In some embodiments, the dihalodiodobenzene compound is selected from 2,3-dibromo-1,4-diiodobenzene 1,2-dibromo-3,6-diiodobenzene, 1,4-dibromo-2,5,-diiodobenzene, 1,3-dibromo-2,5-diiodobenzene, and 1,2-dichloro-3,6-diiodobenzene, 1,4-dichloro-2,5,-diiodobenzene, 1,3-dichloro-2,5-diiodobenzene, or any combination thereof. In some embodiments, the dihalophenyl diboronate compound is 2,3,dibromophenyl-1,4-diboronate and the dihalodiodobenzene compound is 2,3-dibromo-1,4-diiodobenzene.

In some embodiments, coupling a first aryl monomer and a second aryl monomer to provide a linearly conjugated aryl compound intermediate may include contacting the first aryl monomer with the second aryl monomer in a molar ratio of about 2:1 to about 1:2.

In some embodiments, coupling a first aryl monomer and a second aryl monomer to provide a linearly conjugated aryl compound may further include adding at least one catalyst. In some embodiments, the catalyst is a palladium catalyst, a nickel catalyst, or a combination thereof. In some embodiments, the palladium catalyst is tetrakis(triphenylphosphine) palladium, palladium acetate, bis(triphenylphosphine)palladium(II) dichloride and 1,1'-bis(diphenylphosphino)ferrocene]palladium(II) dichloride, palladium(II) acetate tert-alkyl isocyanide, a palladium on carbon, a palladium-silicone dioxide catalyst, palladium nickel triphenylphosphine, palladium chiral disphosphine, palladium 2,2'-bis(diphenylphosphino)-1,1'-binaphthyl, palladium 1,2-bis(diphenylphosphino)ethane, or any combination thereof. In some embodiments, the palladium catalyst is [1,1' bis(diphenylphosphino)ferrocene]palladium(II) dichloride. In some embodiments, the nickel catalyst is nickel triphenylphosphine, nickel chiral disphosphine, nickel 2,2'-bis(diphenylphosphino)-1,1'-binaphthyl, nickel 1,2-bis(diphenylphosphino)ethane, palladium nickel triphenylphosphine, or any combination thereof.

In some embodiments, coupling a first aryl monomer and a second aryl monomer to provide a linearly conjugated aryl compound intermediate may include adding a solvent, an aqueous base, or a combination thereof. In some embodiments, the solvent is an organic solvent, tetrahydrofuran, dimethylformamide, dichloromethane, ethyl acetate, acetone, acetonitrile, dimethyl sulfoxide, propylene carbonate, formic acid, n-butanol, isopropanol, n-propanol, ethanol, methanol, acetic acid, pentane, cyclopentanes, hexane, cyclohexane, benzene, toluene, 1,4-dioxane, chloroform, diethyl ether, heptane dimethoxymethane, or any combination thereof. In some embodiments, the aqueous base is sodium carbonate, sodium hydroxide, potassium hydroxide, barium hydroxide, cesium hydroxide, strontium hydroxide, calcium hydroxide, lithium hydroxide, rubidium hydroxide potassium carbonate, sodium bicarbonate, thallium carbonate, thallium hydroxide, tripotassium phosphate, potassium acetate, a tertiary amine, potassium fluoride, cesium fluoride, tetrabutylammonium fluoride, pyrolidine, piperidine, diisopropylamine, diazabicycloundecene, trisodium phosphate, sodium carbonate, potassium carbonate, cesium acetate, or any combination thereof. In some embodiments, the tertiary amine is triethylamine, N,N-dimethylethanamine, N-ethyl-N-methylethanamine, N-ethyl-N-methyl-3-hexanamine, or any combination thereof.

In some embodiments, coupling a first aryl monomer and a second aryl monomer to provide a linearly conjugated aryl compound intermediate may include heating to a temperature of about 20° C. to about 120° C. for a period of about 1 hour to about 36 hours. In some embodiments, coupling a first aryl monomer and a second aryl monomer to provide a linearly conjugated aryl compound intermediate may include heating to a temperature of about 20° C. to about 40° C., about 40° C. to about 60° C., about 60° C. to about 80° C., about 80° C. to about 100° C., or about 100° C. to about 120° C. Specific examples of temperatures include about 20° C., about 40° C., about 60° C., about 80° C., about 100° C., about 120° C., and ranges between any two of these values (including endpoints). In some embodiments, coupling a first aryl monomer and a second aryl monomer to provide a linearly conjugated aryl compound intermediate may include heating for a period of about 1 hour to about 6 hours, about 6 hours to about 12 hours, about 12 hours to about 18 hours, about 18 hours to about 24 hours, about 24 hours to about 32 hours, or about 32 hours to about 36 hours. In some embodiments, the heating can be performed for more than 36 hours. Specific examples of heating periods include about 1 hour, about 2 hours, about 4 hours, about 6 hours, about 8 hours, about 10 hours, about 12 hours, about 18 hours, about 24 hours, about 32 hours, about 36 hours, and ranges between any two of these values (including endpoints).

Some embodiments may include endcapping the linearly conjugated aryl compound intermediate polycyclization of. In some embodiments, endcapping the linearly conjugated aryl compound intermediate occurs prior the polycyclization of the linearly conjugated aryl compound to provide a graphene nanoribbon precursor. In some embodiments, endcapping the linearly conjugated aryl compound may include coupling the graphene nanoribbon precursor with an aryl monomer of formula (VI):

(VI)

wherein $R_{14}$ is hydrogen, fluorine, chlorine, bromine, iodine, lithium, trifluoromethanesulfonate, mesylate, or tosylate; and wherein $R_{15}$ is hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, or a zinc halide.

In some embodiments, the unsubstituted ring carbons on the aryl monomer of formula VI, may optionally be independently substituted with groups selected from hydrogen, hydroxyl, a substituted or unsubstituted (C1-C20)alkyl, (C1-C20)hydroxyalkyl, (C1-C20)alkoxy, (C1-C20)alkylcarboxy, a substituted or unsubstituted aryl, (C1-C20)haloalkyl, (C2-C6) alkenyl, (C2-C6) alkynyl, or an oxo.

In some embodiments, endcapping the linearly conjugated aryl compound intermediate may include coupling the graphene nanoribbon precursor with a 2-bromophenyl boronate, a 2-chlorophenyl boronate, 2-bromo-1-iodobenzene, 2-chloro-1-iodobenzene, or a combination thereof.

In some embodiments, endcapping the linearly conjugated aryl compound intermediate may include adding a palladium catalyst, a copper salt, an aqueous base, or a combination thereof. In some embodiments, the palladium catalyst is tetrakis(triphenylphosphine) palladium, palladium acetate, bis(triphenylphosphine)palladium(II) dichloride and 1,1'-bis(diphenylphosphino)ferrocene]palladium(II) dichloride, palladium(II) acetate tert-alkyl isocyanide, a palladium on carbon, a palladium-silicone dioxide catalyst, palladium nickel triphenylphosphine, palladium chiral disphosphine, palladium 2,2'-bis(diphenylphosphino)-1,1'-binaphthyl, palladium 1,2-Bis(diphenylphosphino)ethane, or any combination thereof. In some embodiments, the palladium catalyst is tetrakis(triphenylphosphine) palladium. In some embodiments, the copper salt is copper(I) iodide, copper(I) bromide, copper(II) bromide, copper(I) chloride, copper(II) chloride, copper(II) cyclohexanbutyrate, copper (II) fluoride, copper(II) D-gluconate, copper(II) formate, copper(II) hydroxide, copper(II) molybdate, copper(II) nitrate, copper(II) perchlorate, copper(II) pyrophosphate, copper(II) selenite, copper(II) sulfate, copper(II) tartrate, copper(II) tetrafluoroborate, copper(I) thiocyanate, tetra amine copper(II) sulfate, or any combination thereof. In some embodiments, the aqueous base is sodium carbonate, sodium hydroxide, potassium hydroxide, barium hydroxide, cesium hydroxide, strontium hydroxide, calcium hydroxide, lithium hydroxide, rubidium hydroxide potassium carbonate, sodium bicarbonate, thallium carbonate, thallium hydroxide, tripotassium phosphate, potassium acetate, a tertiary amine, potassium fluoride, cesium fluoride, tetrabutylammonium fluoride, pyrrolidine, piperidine, diisopropylamine, diazabicycloundecene, trisodium phosphate, sodium carbonate, potassium carbonate, cesium acetate, or any combination thereof.

In some embodiments, endcapping the linearly conjugated aryl compound intermediate may include heating to a temperature of about 20° C. to about 150° C. for about 1 hour to about 36 hours. In some embodiments, endcapping the linearly conjugated aryl compound intermediate may include heating to a temperature of about 20° C. to about 40° C., about 40° C. to about 60° C., about 60° C. to about 80° C., about 80° C. to about 100° C., about 100° C. to about 120° C., about 120° C. to about 140° C., or about 140° C. to about 150° C. Specific examples of temperatures include about 20° C., about 40° C., about 60° C., about 80° C., about 100° C., about 110° C., about 120° C., about 130° C., about 140° C., about 150° C., and ranges between any two of these values (including endpoints). In some embodiments, endcapping the linearly conjugated aryl compound intermediate may include heating for a period of about 1 hour to about 6 hours, about 6 hours to about 12 hours, about 12 hours to about 18 hours, about 18 hours to about 24 hours, about 24 hours to about 32 hours, or about 32 hours to about 36 hours. In some embodiments, the heating can be performed for more than 36 hours. Specific examples of heating periods include about 1 hour, about 2 hours, about 4 hours, about 6 hours, about 8 hours, about 10 hours, about 12 hours, about 18 hours, about 24 hours, about 32 hours, about 36 hours, and ranges between any two of these values (including endpoints).

In some embodiments, endcapping is performed in a single reaction vessel by adding compound VI directly to the completed coupling of a first aryl monomer and a second aryl monomer to provide a linearly conjugated aryl compound intermediate.

In some embodiments, polycyclization of the linearly conjugated aryl compound to provide a graphene nanoribbon precursor may include contacting the conjugated aryl compound with a catalyst. In some embodiments, the catalyst is a platinum catalyst, a palladium catalyst, a silver catalyst, a gold catalyst, a ruthenium catalyst, a gallium catalyst, an indium catalyst, an iron salt catalyst, or any combination thereof. In some embodiments, the catalyst is platinum (II) chloride, palladium chloride, tetrakis(triphenylphosphine) palladium, palladium acetate, bis(triphenylphosphine)palladium(II) dichloride, 1,1'-bis(diphenylphosphino)ferrocene]palladium(II) dichloride, palladium(II) acetate tert-alkyl isocyanide, a palladium on carbon, a palladium-silicone dioxide catalyst, palladium nickel triphenylphosphine, palladium chiral disphosphine, palladium 2,2'-bis(diphenylphosphino)-1,1'-binaphthyl, palladium 1,2-bis(diphenylphosphino)ethane, gold (III) chloride, gallium (III) chloride, indium (III) chloride, iron (III) chloride, iron tris(trifluoromethanesulfonate), or any combination thereof.

Some embodiments may include coupling the linearly conjugated aryl compound intermediate with a mono-substituted acetylene compound to form the linearly conjugated aryl compound, wherein the mono-substituted acetylene compound has a formula (IV):

$$R_{12}\text{———}R_{13} \quad (IV)$$

wherein $R_{12}$ is hydrogen, aryl, polycyclic aryl, alkyl, copper, zinc, magnesium, tin, boron, silicon, indium, aluminum, lithium, sodium, zinc chloride, mercury chloride, manganese (II) chloride, magnesium bromide, or bis(cyclopentadienyl)dimethyl zirconium; and $R_{13}$ is hydrogen, trimethylsilyl, tert-butyldimethylsilyl, tert-butyldiphenylsilyl, triethylsilyl, triisopropylsilyl, alkyl, phenyl, furanyl, thiophenyl, pyridyl, or poly (m-phenylene) comprising about 2 to about 20 m-phenylene units. In some embodiments, $R_{13}$ is hydrogen and $R_{14}$ is trimethylsilyl.

In some embodiments, coupling the linearly conjugated aryl compound intermediate with a mono-substituted acetylene compound to form the linearly conjugated aryl compound may include adding at least one solvent. In some embodiments, the solvent is tetrahydrofuran, dimethylformamide, dichloromethane, ethyl acetate, acetone, acetonitrile, dimethyl sulfoxide, propylene carbonate, formic acid, n-butanol, isopropanol, n-propanol, ethanol, methanol, acetic acid, pentane, cyclopentanes, hexane, cyclohexane, benzene, toluene, 1,4-dioxane, chloroform, diethyl ether, heptane dimethoxymethane, or any combination thereof.

In some embodiments, coupling the linearly conjugated aryl compound intermediate with a mono-substituted acetylene compound to form the linearly conjugated aryl compound may further include contacting the linearly conjugated aryl compound with a fluoride source. In some embodiments, the fluoride source is tetrabutylammonium fluoride, sodium fluoride, potassium fluoride, hydrogen fluoride or any combination thereof.

In some embodiments, polycyclization of the linearly conjugated aryl compound to provide a graphene nanoribbon precursor may include adding at least one solvent. In some embodiments, the solvent is tetrahydrofuran, dimethylformamide, dichloromethane, dichloroethane, ethyl acetate, acetone, acetonitrile, dimethyl sulfoxide, propylene carbonate, formic acid, n-butanol, isopropanol, n-propanol, ethanol, methanol, acetic acid, pentane, cyclopentanes, hexane, cyclohexane, benzene, toluene, 1,4-dioxane, chloroform, diethyl ether, heptane dimethoxymethane, or any combination thereof.

In some embodiments, polycyclization of the linearly conjugated aryl compound to provide a graphene nanoribbon precursor may include heating to a temperature of about 20° C. to about 150° C. for about 1 hour to about 36 hours. In some embodiments, polycyclization of the linearly conjugated aryl compound to provide a graphene nanoribbon precursor may include heating to a temperature of about 20° C. to about 40° C., about 40° C. to about 60° C., about 60° C. to about 80° C., about 80° C. to about 100° C., about 100° C. to about 120° C., about 120° C. to about 140° C., or about 140° C. to about 150° C. Specific examples of temperatures include about 20° C., about 40° C., about 60° C., about 80° C., about 100° C., about 110° C., about 120° C., about 130° C., about 140° C., about 150° C., and ranges between any two of these values (including endpoints). In some embodiments, polycyclization of the linearly conjugated aryl compound to provide a graphene nanoribbon precursor may include heating for a period of about 1 hour to about 6 hours, about 6 hours to about 12 hours, about 12 hours to about 18 hours, about 18 hours to about 24 hours, about 24 hours to about 32 hours, or about 32 hours to about 36 hours. In some embodiments, the heating can be performed for more than 36 hours. Specific examples of heating periods include about 1 hour, about 2 hours, about 4 hours, about 6 hours, about 8 hours, about 10 hours, about 12 hours, about 18 hours, about 24 hours, about 32 hours, about 36 hours, and ranges between any two of these values (including endpoints).

In some embodiments, polycyclization of the linearly conjugated aryl compound to provide a graphene nanoribbon precursor may further comprise performing a alkyne cyclization of the linearly conjugated aryl compound. For example, in some embodiments, iodine monochloride and a solvent are added to the linearly conjugated aryl compound and cooled to about −78° C. In some embodiments, the mixture is stirred for about 1 hour. In some embodiments, the resulting product is treated with sodium thiosulfate solution and extracted with a solvent such as, but not limited to toluene. In some embodiments, the resulting product is treated with n-butyl lithium in the presence of a solvent such as but not limited to tetrahydrofuran and cooled to about −78° C. In some embodiments, after cooling the product and n-butyl lithium mixture, an excess of a solvent such as, but not limited to, methanol is added followed by addition of a second solvent such as but not limited to dichloromethane to produce the graphene nanoribbon precursor. In some embodiments the graphene nanoribbon precursor is washed with a mineral acid such as, but not limited to hydrochloric acid, a base such as, but not limited to ammonium hydroxides solution, and water.

Some embodiments may include cyclodehydrogenation of the graphene nanoribbon precursor to provide a graphene nanoribbon. In some embodiments, the cyclodehydrogenation of the graphene nanoribbon precursor to provide a graphene nanoribbon may include oxidative cyclodehydrogenation of the graphene nanoribbon precursor. In some embodiments, cyclodehydrogenation the graphene nanoribbon precursor to provide a graphene nanoribbon may include contacting the graphene nanoribbon precursor with iron (III) chloride, molybdenum (V) chloride, copper (II) chloride, copper (II) triflate, aluminum (III) chloride, titanium (IV) chloride, phenyliodide bis(trifluoroacetate), boron trifluoride etherate, lead (IV) acetate, tellurium (III) triflate, trifluoroacetic acid or any combination thereof.

In some embodiments, cyclodehydrogenation of the graphene nanoribbon precursor to provide a graphene nanoribbon may include adding at least one first solvent. In some embodiments, the at least one first solvent is nitromethane, tetrahydrofuran, dimethylformamide, dichloromethane, dichloroethane, ethyl acetate, acetone, acetonitrile, dimethyl sulfoxide, propylene carbonate, formic acid, n-butanol, isopropanol, n-propanol, ethanol, methanol, acetic acid, pentane, cyclopentanes, hexane, cyclohexane, benzene, toluene, 1,4-dioxane, chloroform, diethyl ether, heptane dimethoxymethane, carbon disulfide, or any combination thereof.

In some embodiments, cyclodehydrogenation of the graphene nanoribbon precursor to provide a graphene nanoribbon may include adding a second solvent. In some embodiments, the second solvent is methanol, tetrahydrofuran, dimethylformamide, dichloromethane, ethyl acetate, acetone, acetonitrile, dimethyl sulfoxide, propylene carbonate, formic acid, n-butanol, isopropanol, n-propanol, ethanol, methanol, acetic acid, pentane, cyclopentanes, hexane, cyclohexane, benzene, toluene, 1,4-dioxane, chloroform, diethyl ether, heptane dimethoxymethane, carbon disulfide, or any combination thereof.

In some embodiments, the graphene nanoribbon produced by the methods described herein may have a width of about 5 nm. In some embodiments, the graphene nanoribbon produced by the methods described herein has a carrier mobility of about 1 cm2/V·s to about 500 cm2/V·s. In some embodiments, the graphene nanoribbon produced by the methods described herein has a width of about 0.5 nm to about 7 nm. In some embodiments, the graphene nanoribbon produced by the methods described herein has a width of about 0.5 nm to about 5 nm. In some embodiments, the graphene nanoribbon produced by the methods described herein has a width of about 1.5 nm to about 6.6 nm.

Methods for Synthesizing a Graphene Nanoribbon Having a Zigzag Backbone

Some embodiments are directed to a method of synthesizing a graphene nanoribbon having a zigzag backbone. The method may include providing a zigzag conjugated aryl compound having a formula (VI):

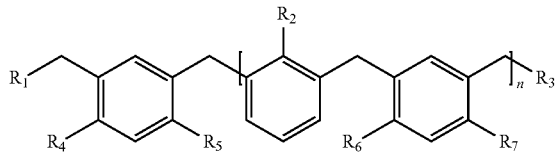

(VI)

wherein $R_1$ and $R_3$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide; wherein $R_2$ is selected from a hydrogen, trimethylsilyl, tert-butyldimethylsilyl, tert-butyldiphenylsilyl, triethylsilyl, triisopropylsilyl, alkyl, phenyl, furanyl, thiophenyl, pyridyl, or poly (m-phenylene) including about 2 to about 20 m-phenylene units; wherein $R_4$ to $R_7$ are independently selected from an aldehyde group and an acetal group; and polycyclization of the zigzag conjugated aryl compound to provide a graphene nanoribbon precursor.

Some embodiments may include coupling a first aryl monomer and a second aryl monomer to provide a zigzag conjugated aryl compound intermediate. In some embodiments, the first aryl monomer has a formula (VII):

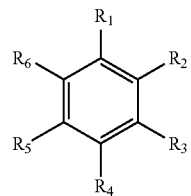

(VII)

wherein $R_1$ is hydrogen, trimethylsilyl, tert-butyldimethylsilyl, tert-butyldiphenylsilyl, triethylsilyl, triisopropylsilyl, alkyl, phenyl, furanyl, thiophenyl, pyridyl, or poly (m-phenylene) including about 2 to about 20 m-phenylene units; wherein $R_2$ to $R_6$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide wherein at least two of $R_2$ to $R_6$ are not hydrogen; and wherein the second aryl monomer has a formula (VIII):

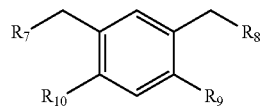

(VIII)

wherein $R_7$ and $R_8$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide; and wherein $R_9$ and $R_{10}$ are independently selected from an aldehyde group, and an acetal group.

Some embodiments may include coupling a first aryl monomer and a second aryl monomer to provide a zigzag conjugated aryl compound intermediate wherein the first aryl monomer is 2-trimethylsilyl-1,3-diboronic acid and the second aryl monomer is 4,6-bis(bromomethyl)isophthaladehyde.

In some embodiments, coupling a first aryl monomer and a second aryl monomer to provide a zigzag conjugated aryl compound intermediate may include contacting the first aryl monomer with the second aryl monomer in a molar ratio of about 2:1 to about 1:2.

In some embodiments, coupling a first aryl monomer and a second aryl monomer to provide a zigzag conjugated aryl compound may include adding at least one catalyst. In some embodiments, the catalyst is a palladium catalyst, a nickel catalyst, or a combination thereof. In some embodiments, the palladium catalyst is tetrakis(triphenylphosphine) palladium, palladium acetate, bis(triphenylphosphine)palladium (II) dichloride and 1,1'-bis(diphenylphosphino)ferrocene] palladium(II) dichloride, palladium(II) acetate tert-alkyl isocyanide, a palladium on carbon, a palladium-silicone dioxide catalyst, palladium nickel triphenylphosphine, palladium chiral disphosphine, palladium 2,2'-bis(diphenylphosphino)-1,1'-binaphthyl, palladium 1,2-Bis(diphenylphosphino)ethane, or any combination thereof. In some embodiments, the palladium catalyst is [1,1' bis(diphenylphosphino)ferrocene]palladium(II) dichloride. In some embodiments, the nickel catalyst is nickel triphenylphosphine, nickel chiral disphosphine, nickel 2,2'-bis(diphenylphosphino)-1,1'-binaphthyl, nickel 1,2-Bis(diphenylphosphino)ethane, palladium nickel triphenylphosphine, or any combination thereof.

In some embodiments, coupling a first aryl monomer and a second aryl monomer to provide a zigzag conjugated aryl compound further may include adding a solvent, an aqueous base, a fluoride source, or a combination thereof. In some embodiments, the solvent is an organic solvent, tetrahydrofuran, dimethylformamide, dichloromethane, ethyl acetate, acetone, acetonitrile, dimethyl sulfoxide, propylene carbonate, formic acid, n-butanol, isopropanol, n-propanol, ethanol, methanol, acetic acid, pentane, cyclopentanes, hexane, cyclohexane, benzene, toluene, 1,4-dioxane, chloroform, diethyl ether, heptane dimethoxymethane, or any combination thereof. In some embodiments, the aqueous base is sodium carbonate, sodium hydroxide, potassium hydroxide, barium hydroxide, cesium hydroxide, strontium hydroxide, calcium hydroxide, lithium hydroxide, rubidium hydroxide potassium carbonate, sodium bicarbonate, thallium carbonate, thallium hydroxide, tripotassium phosphate, potassium acetate, a tertiary amine, potassium fluoride, cesium fluoride, tetrabutylammonium fluoride, pyrolidine, piperidine, diisopropylamine, diazabicycloundecene, trisodium phosphate, sodium carbonate, potassium carbonate, cesium acetate, or any combination thereof. In some embodiments, the tertiary amine is triethylamine, N,N-dimethylethanamine, N-ethyl-N-methylethanamine, N-ethyl-N-methyl-3-hexanamine, or any combination thereof.

In some embodiments, coupling a first aryl monomer and a second aryl monomer to provide a zigzag conjugated aryl compound may include heating to a temperature of about 20° C. to about 120° C. for a period of about 1 hour to about 36 hours. In some embodiments, coupling a first aryl monomer and a second aryl monomer to provide a zigzag conjugated aryl compound may include heating to a temperature of about 20° C. to about 40° C., about 40° C. to about 60° C., about 60° C. to about 80° C., about 80° C. to about 100° C., or about 100° C. to about 120° C. Specific examples of temperatures include about 20° C., about 40° C., about 60° C., about 80° C., about 100° C., about 110° C., about 120° C., and ranges between any two of these values (including endpoints). In some embodiments, coupling a first aryl monomer and a second aryl monomer to provide a zigzag conjugated aryl compound may include heating for a period of about 1 hour to about 6 hours, about 6 hours to about 12 hours, about 12 hours to about 18 hours, about 18 hours to about 24 hours, about 24 hours to about 32 hours, or about 32 hours to about 36 hours. In some embodiments, the heating can be performed for more than 36 hours. Specific examples of heating periods include about 1 hour, about 2 hours, about 4 hours, about 6 hours, about 8 hours, about 10 hours, about 12 hours, about 18 hours, about 24 hours, about 32 hours, about 36 hours, and ranges between any two of these values (including endpoints).

Some embodiments may include endcapping the zigzag conjugated aryl compound prior to polycyclization of the zigzag conjugated aryl compound to form a graphene nanoribbon precursor. In some embodiments, endcapping the zigzag conjugated aryl compound intermediate occurs prior the polycyclization of the zigzag conjugated aryl compound to provide a graphene nanoribbon precursor. In some embodiments, endcapping the zigzag conjugated aryl compound may include coupling the graphene nanoribbon precursor with an aryl monomer of formula (XI):

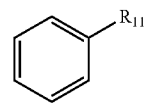

wherein $R_{11}$ is hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, or a zinc halide.

In some embodiments, the unsubstituted ring carbons on the aryl monomer of formula XI, may optionally be independently substituted with a group selected from hydrogen, hydroxyl, a substituted or unsubstituted (C1-C20)alkyl, (C1-C20)hydroxyalkyl, (C1-C20)alkoxy, (C1-C20)alkylcarboxy, a substituted or unsubstituted aryl, (C1-C20)haloalkyl, C2-C6 alkenyl, C2-C6 alkynyl, or an oxo.

In some embodiments, endcapping the zigzag conjugated aryl compound may include coupling the zigzag conjugated aryl compound with a 2-bromophenyl boronate, a 2-chlorophenyl boronate or a combination thereof.

In some embodiments, endcapping the zigzag conjugated aryl compound may include adding a palladium catalyst, a copper salt, an aqueous base, or a combination thereof. In some embodiments, the palladium catalyst is tetrakis(triphenylphosphine) palladium, palladium acetate, bis(triphenylphosphine)palladium(II) dichloride and 1,1'-bis(diphenylphosphino)ferrocene]palladium(II) dichloride, palladium(II) acetate tert-alkyl isocyanide, a palladium on carbon, a palladium-silicone dioxide catalyst, palladium nickel triphenylphosphine, palladium chiral disphosphine, palladium 2,2'-bis(diphenylphosphino)-1,1'-binaphthyl, palladium 1,2-Bis(diphenylphosphino)ethane, or any combination thereof. In some embodiments, the palladium catalyst is tetrakis (triphenylphosphine) palladium. In some embodiments, the copper salt is copper(I) iodide, copper(I) bromide, copper(II) bromide, copper(I) chloride, copper(II) chloride, copper(II) cyclohexanbutyrate, copper(II) fluoride, copper(II) D-gluconate, copper(II) formate, copper(II) hydroxide, copper(II) molybdate, copper(II) nitrate, copper(II) perchlorate, copper (II) pyrophosphate, copper(II) selenite, copper(II) sulfate, copper(II) tartrate, copper(II) tetrafluoroborate, copper(I) thiocyanate, tetra amine copper(II) sulfate, or any combination thereof. In some embodiments, the aqueous base is sodium carbonate, sodium hydroxide, potassium hydroxide, barium hydroxide, cesium hydroxide, strontium hydroxide, calcium hydroxide, lithium hydroxide, rubidium hydroxide potassium carbonate, sodium bicarbonate, thallium carbonate, thallium hydroxide, tripotassium phosphate, potassium acetate, a tertiary amine, potassium fluoride, cesium fluoride, tetrabutylammonium fluoride, pyrolidine, piperidine, diisopropylamine, diazabicycloundecene, trisodium phosphate, sodium carbonate, potassium carbonate, cesium acetate, or any combination thereof.

In some embodiments, endcapping the zigzag conjugated aryl compound may include heating to a temperature of about 20° C. to about 150° C. for about 1 to about 36 hours. In some embodiments, endcapping the zigzag conjugated aryl compound may include heating to a temperature of about 20° C. to about 40° C., about 40° C. to about 60° C., about 60° C. to about 80° C., about 80° C. to about 100° C., about 100° C. to about 120° C., about 120° C. to about 140° C. or about 140° C. to about 150° C. Specific examples of temperatures include about 20° C., about 40° C., about 60° C., about 80° C., about 100° C., about 110° C., about 120° C., about 130° C., about 140° C., about 150° C., and ranges between any two of these values (including endpoints). In some embodiments, endcapping the zigzag conjugated aryl compound may include heating for a period of about 1 hour to about 6 hours, about 6 hours to about 12 hours, about 12 hours to about 18 hours, about 18 hours to about 24 hours, about 24 hours to about 32 hours, or about 32 to about 36 hours. In some embodiments, the heating can be performed for more than 36 hours. Specific examples of heating periods include about 1 hour, about 2 hours, about 4 hours, about 6 hours, about 8 hours, about 10 hours, about 12 hours, about 18 hours, about 24 hours, about 32 hours, about 36 hours, and ranges between any two of these values (including endpoints).

In some embodiments, polycyclization of the zigzag conjugated aryl compound to provide a graphene nanoribbon precursor may include contacting the conjugated aryl compound with tosylamine, and at least one Lewis acid. In some embodiments, the Lewis acid is boron trifluoride etherate, scandium trifluoromethanesulfonate, bromotricarbonyl(tetrahydrofuran)rhenium(I) dimer, bromopentacarbonylrhenium(I), dirhenium decacarbonyl, bromopentacarbonylmanganese, dimaganese decacarbonyl, iron (III) chloride, aluminum chloride, chloro(1,5-cyclooctadiene)iridium(I) dimer, copper(II) trifluoromethanesulfonate, silver trifluoromethanesulfonate, indium chloride, indium (III) trifluoromethanesulfonate, bismuth (III) trifluoromethanesulfonate, or scandium (III) trifluoromethanesulfonate.

In some embodiments, polycyclization of the zigzag conjugated aryl compound to provide a graphene nanoribbon precursor may include adding at least one solvent. In some embodiments, the solvent is tetrahydrofuran, dimethylformamide, dichloromethane, ethyl acetate, acetone, acetonitrile, dimethyl sulfoxide, propylene carbonate, formic acid, n-butanol, isopropanol, n-propanol, ethanol, methanol, acetic acid, pentane, cyclopentanes, hexane, cyclohexane, benzene, toluene, 1,4-dioxane, chloroform, diethyl ether, heptane dimethoxymethane, or any combination thereof.

Some embodiments may include removing $R_2$ from the graphene nanoribbon precursor to provide a zigzag graphene nanoribbon. In some embodiments, removal of $R_2$ from the graphene nanoribbon precursor may include contacting the graphene nanoribbon precursor with at least one fluoride source. In some embodiments, the fluoride source is tetrabutylammonium fluoride, hydrogen fluoride, or a combination thereof.

Graphene Nanoribbons and Uses Thereof

Some embodiments are directed to a compound having the structure of the following formula (XII):

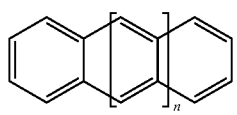

(XII)

wherein n is an integer of about 5 to about 100,000. In some embodiments, the compound has a carrier mobility of about 1 cm$^2$/V·s to about 500 cm$^2$/V·s. In some embodiments, the compound has a carrier mobility of about 25 cm$^2$/V·s. In some embodiments, the compound has a width of about 0.3 nm.

Some embodiments are directed to a transistor comprising the compound of structure XII. In some embodiments, the transistor is a field effect transistor, a bipolar junction transistor, a diffusion transistor, a unijunction transistor, a single-electron transistor, a nanofluidic transistor, a tetrode transistor, a pentode transistor, a trigate transistor, a junctionless nanowire transistor, or a vacuum channel transistor.

Some embodiments are directed to a transistor comprising the compound of structure XII. In some embodiments, transistors comprising the compound of structure XII can be used as conductors and semiconductors for use in transistors including but not limited to organic thin film transistors and field effect transistors. In some embodiments, transistors comprising the compound of structure XII can be used as conductors and semiconductors for use in miniaturized devices such as but not limited to microelectromechanical systems (MEMS) and nanoelectromechanical systems (NEMS). In some embodiments transistors comprising the compound of structure XII can be used as sensing elements in sensor devices including but not limited to gas sensors.

Some embodiments are directed a compound having a structure of the following formula (XIII):

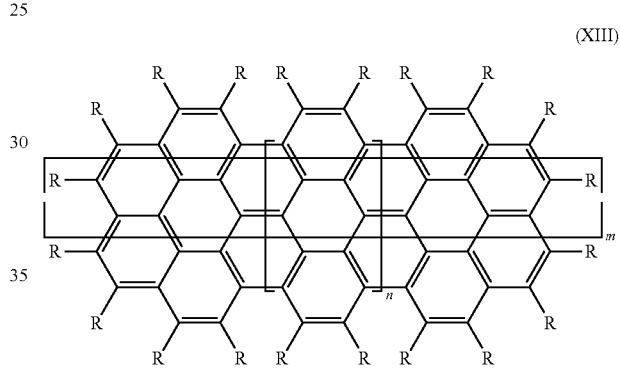

(XIII)

wherein n is an integer of about 5 to about 100,000, m is an integer of 0 to 20, and wherein each R is independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms and wherein the alkyl groups may be combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms, or a cyano group. In some embodiments, each R is a hydrogen atom. In some embodiments, the compound has a carrier mobility of about 1 cm$^2$/V·s to about 500 cm$^2$/V·s.

Some embodiments are directed to a transistor comprising the compound of structure XIII. In some embodiments, the transistor is a field effect transistor, a bipolar junction transistor, a diffusion transistor, a unijunction transistor, a single-electron transistor, a nanofluidic transistor, a tetrode transistor, a pentode transistor, a trigate transistor, a junctionless nanowire transistor, or a vacuum channel transistor.

Some embodiments are directed to an organic thin film transistor comprising: a substrate; and a gate electrode, a source electrode and a drain electrode, an insulator layer and an organic semiconductor layer being provided on the substrate; a source-drain cover controllable by applying a voltage to the gate electrode whereby the organic thin film transistor performs and on-off operation; and wherein the semiconductor layer may include a compound of formula (XIV):

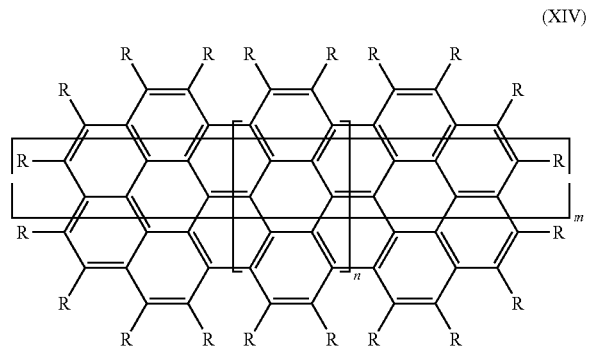

(XIV)

wherein n is an integer of about 5 to about 100,000, m is an integer of 0 to about 20, and wherein each R is independently a hydrogen atom, a halogen atom, an alkyl group having 1 to 30 carbon atoms, a haloalkyl group having 1 to 30 carbon atoms, an alkoxy group having 1 to 30 carbon atoms, a haloalkoxy group having 1 to 30 carbon atoms, an alkylthio group having 1 to 30 carbon atoms, a haloalkylthio group having 1 to 30 carbon atoms, an alkylamino group having 1 to 30 carbon atoms, a dialkylamino group having 2 to 60 carbon atoms and wherein the alkyl groups may be combined with each other to form a ring structure containing the nitrogen atom, an alkylsulfonyl group having 1 to 30 carbon atoms, a haloalkylsulfonyl group having 1 to 30 carbon atoms, an aromatic hydrocarbon group having 6 to 60 carbon atoms, an aromatic heterocyclic group having 3 to 60 carbon atoms, an alkylsilyl group having 3 to 20 carbon atoms, an alkylsilylacetylene group having 5 to 60 carbon atoms, or a cyano group. In some embodiments, each R is a hydrogen atom.

In some embodiments, the source electrode and the drain electrode are formed on the substrate such that they are opposed to each other; the organic semiconductor layer is formed so as to cover the source electrode, the drain electrode or a combination thereof; the insulating layer is formed so as to cover the semiconductor layer; and wherein the gate electrode is formed above the insulating layer. In some embodiments, the source electrode and drain electrode are opposed to each other with a pre-determined interval to form a gap; wherein the organic semiconductor layer is formed so as to cover the gap.

In some embodiments, the gate electrode is formed on the substrate; the insulating layer is formed so as to cover the gate electrode and the substrate; and wherein the source electrode and drain electrode are formed on the insulating layer and wherein the organic semiconductor layer is formed to cover the source electrode and the drain electrode.

In some embodiments, the compound has a carrier mobility of greater than about 10 cm$^2$/V·s.

Some embodiments are directed to an apparatus comprising the organic thin film transistors described herein.

Some embodiments are directed to an organic thin film transistor that may include a substrate; and a gate electrode, a source electrode and a drain electrode, an insulator layer and an organic semiconductor layer being provided on the substrate; a source-drain cover controllable by applying a voltage to the gate electrode whereby the organic thin film transistor performs and on-off operation; and wherein the semiconductor layer may include a compound of formula (XV):

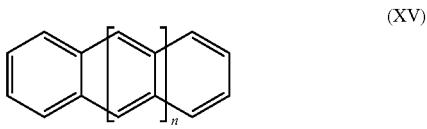

(XV)

wherein n is an integer of 0 to about 100,000.

In some embodiments, the source electrode and the drain electrode are formed on the substrate such that they are opposed to each other; the organic semiconductor layer is formed so as to cover the source electrode, the drain electrode or a combination thereof; the insulating layer is formed so as to cover the semiconductor layer; and wherein the gate electrode is formed above the insulating layer. In some embodiments, the source electrode and drain electrode are opposed to each other with a pre-determined interval to form a gap; wherein the organic semiconductor layer is formed so as to cover the gap.

In some embodiments, the gate electrode is formed on the substrate; the insulating layer is formed so as to cover the gate electrode and the substrate; and wherein the source electrode and drain electrode are formed on the insulating layer and wherein the organic semiconductor layer is formed to cover the source electrode and the drain electrode.

In some embodiments, the compound has a carrier mobility of greater than about 10 cm$^2$/V·s.

In some embodiments, the compounds described herein can be used as reinforcement components in composite lightweight materials. In some embodiments, the compounds described herein can be used where carbon fiber would normally be used such as, but not limited to carbon-fiber reinforced polymers, carbon fiber reinforced plastic and carbon fiber reinforced thermoplastics. Uses for graphene nanoribbon-reinforced materials include but are not limited to watercrafts, rowing shells, bicycles, motorcycles, automobiles, aircraft, and spacecraft, where a high strength-to-weight ratio and very good rigidity are important. Additional uses include but are not limited to small consumer goods such as consumer electronics, tripods, fishing rods, hockey sticks, paintball equipment, archery equipment, tent poles, racquet frames, stringed instrument bodies, drum shells, golf clubs, helmets, pool cues and other sporting goods.

Other uses include, but are not limited to, reinforcing concrete structures, as pre-stressing materials and as chemically resistant coatings.

Some embodiments are directed to an apparatus comprising the organic thin film transistors described herein. In some embodiments, transistors comprising the compounds described herein can be used as conductors and semiconductors for use in transistors including but not limited to organic thin film transistors and field effect transistors. In some embodiments, transistors comprising the compounds described herein can be used as conductors and semiconductors for use in miniaturized devices such as but not limited to microelectromechanical systems (MEMS) and nanoelectromechanical systems (NEMS). In some embodiment's transistors comprising the compounds described herein can be used as sensing elements in sensor devices including but not limited to gas sensors.

In some embodiments, the compounds described herein can be used to form thin films with electron mobility's comparable to, or higher than electron mobility measured for the currently available small molecule and polymeric OTFTs.

EXAMPLES

Example 1—Synthesis of a Graphene Nanoribbon

As shown in Reaction Scheme A, a mixture of 1 equivalent 2,3-dibromobenzene-1,4,-diboronate (1), 1.02 equivalents 2,3-dibromo-1,4-diiodobenzene (2), 0.2 equivalents tetrakistriphenylphosphine palladium, dimethoxyethane, and 2M aqueous sodium carbonate solution (6 equivalents) is heated at 70° C. for 8 hours. To this reaction mixture containing intermediate 3 is added 0.05 equivalents 2-bromophenylboronic acid pinacol and the mixture is heated at 70° C. for 8 hours. After filtering, the filtrate is concentrated under reduced and the residue is washed with water and then with methanol to yield crude intermediate 4 wherein n is an integer of 1 to 100,000. A mixture of 1 monomer equivalent intermediate 4, triethylamine as solvent, 0.05 equivalents tetrakistriphenylphosphine palladium, 2 equivalents copper

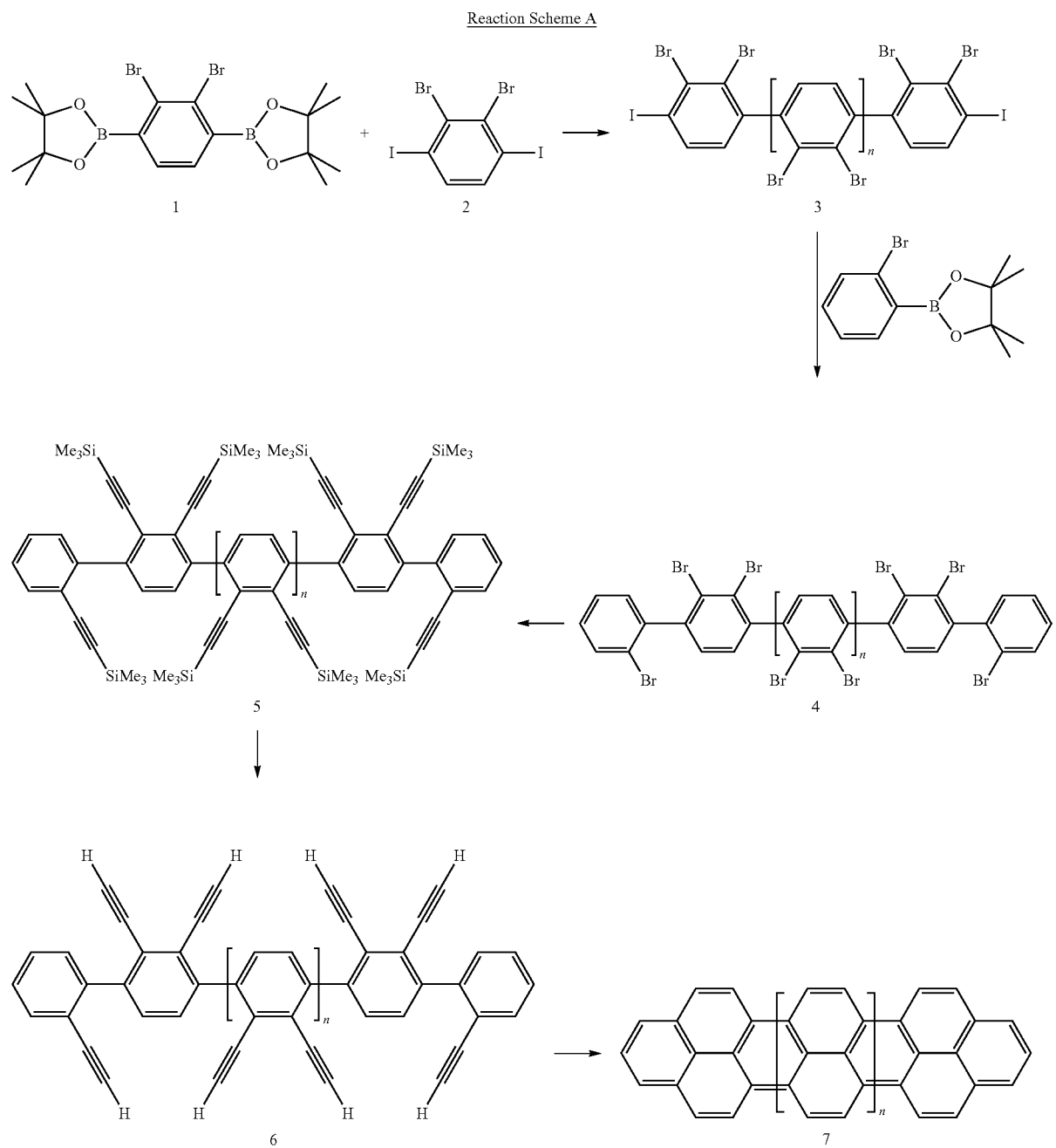

(I) iodide, and 5 equivalents trimethylsilylacetylene is heated at 80° C. for 16 hours. The mixture is filtered and the filtrate is concentrated under reduced pressure. The residue is washed with methanol and then with heptane to provide crude intermediate 5. A mixture of 1 monomer equivalent intermediate 5, 2.2 equivalents tetrabutylammonium fluoride, and tetrahydrofuran is stirred in an ice bath for 2 hours. Water is added and the product is extracted with toluene. The extract is dried over magnesium sulfate and concentrated under reduced pressure to provide intermediate 6. A mixture of 1 monomer equivalent intermediate 6, 0.05 equivalents platinum chloride, and toluene and heated at 120° C. for 20 hours. The mixture is filtered and the filtrate is evaporated under reduced pressure to yield graphene nanoribbon (7).

Example 2—Synthesis of a Graphene Nanoribbon

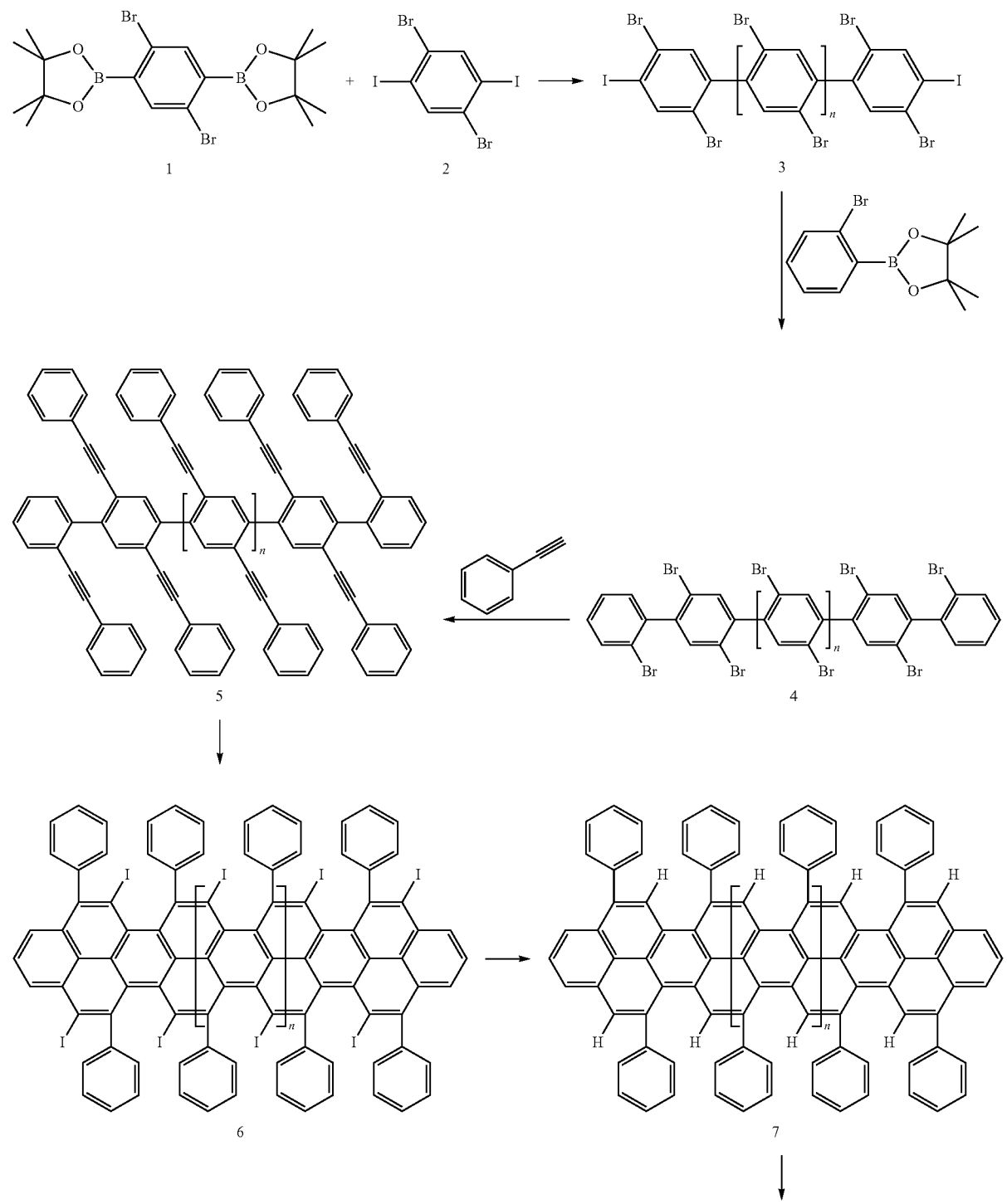

Reaction Scheme B

-continued

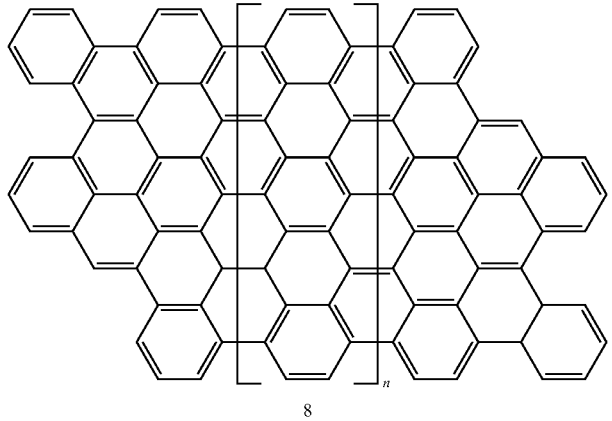

8

As shown in Reaction Scheme B, a mixture of 1 equivalent 2,5-dibromobenzene-1,4,-diboronate (1), 1.02 equivalents 2,5-dibromo-1,4-diiodobenzene (2), 0.2 equivalents tetrakistriphenylphosphine palladium, dimethoxyethane, and 2M aqueous sodium carbonate solution (6 equivalents) is heated at 70° C. for 8 hours. To this reaction mixture containing intermediate 3 is added 0.05 equivalents 2-bromophenylboronic acid pinacol ester is added and the mixture is heated at 70° C. for 8 hours. After filtering, the filtrate is concentrated under reduced pressure and the residue is washed with water and then with methanol to yield crude intermediate 4 wherein n is an integer of 1 to 100,000. A mixture of 1 monomer equivalent intermediate 4, triethylamine as solvent, 0.05 equivalents tetrakistriphenylphosphine palladium, 2 equivalents copper (I) iodide, and 5 equivalents phenylacetylene is heated at 80° C. for 16 hours. The mixture is filtered and the filtrate is concentrated under reduced pressure. The residue is washed with methanol and then with heptane to provide crude intermediate 5. A solution of 2.2 equivalents iodine monochloride is added slowly to a solution of 1 monomer equivalent intermediate 5 in dichloromethane cooled at −78° C. After stirring at −78° C. for 1 hour, the mixture is treated with excess saturated aqueous sodium thiosulfate solution and then extracted with toluene. The extract is dried over magnesium sulfate and concentrated under reduced pressure to provide intermediate 6. A 2.5 M solution of n-butyl lithium in hexanes (2.2 equivalents) is added slowly to a solution of 1 monomer equivalent of 6 in tetrahydrofuran cooled at −78° C. After 5 minutes, excess methanol is added followed by dichloromethane. The mixture is washed with 5% aqueous hydrochloric acid solution, washed with water, and then dried over magnesium sulfate. Evaporation of solvents under reduced pressure yields intermediate 7. To a mixture of 1 monomer equivalent intermediate 7 and dichloromethane is added 25 equivalents of iron (III) chloride in nitromethane. After stirring for 20 hours at ambient temperature, the mixture is treated with methanol. The precipitate is filtered and washed in sequence with water, 5% hydrochloric acid solution, 25% ammonium hydroxide solution, water, methanol and pentane and then dried to under reduced pressure to yield graphene nanoribbon (8).

Example 3—Synthesis of Graphene Nanoribbon

Reaction Scheme C

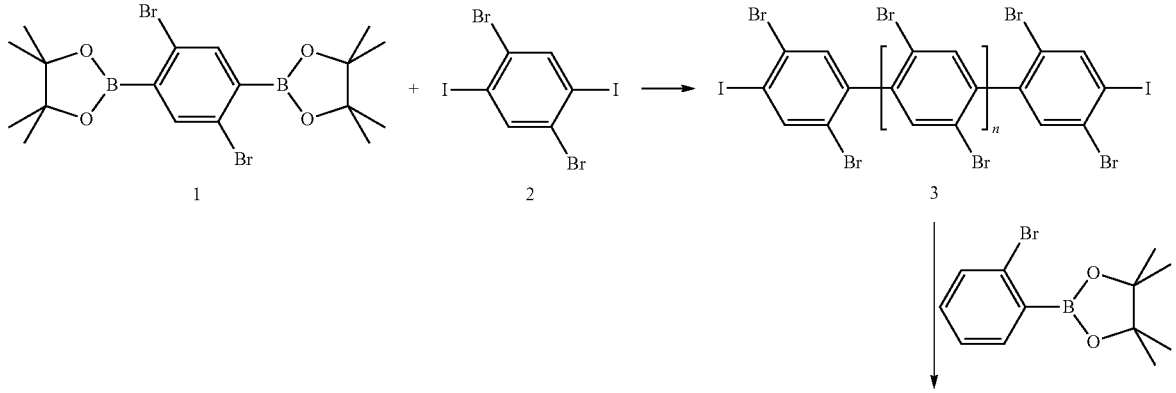

-continued
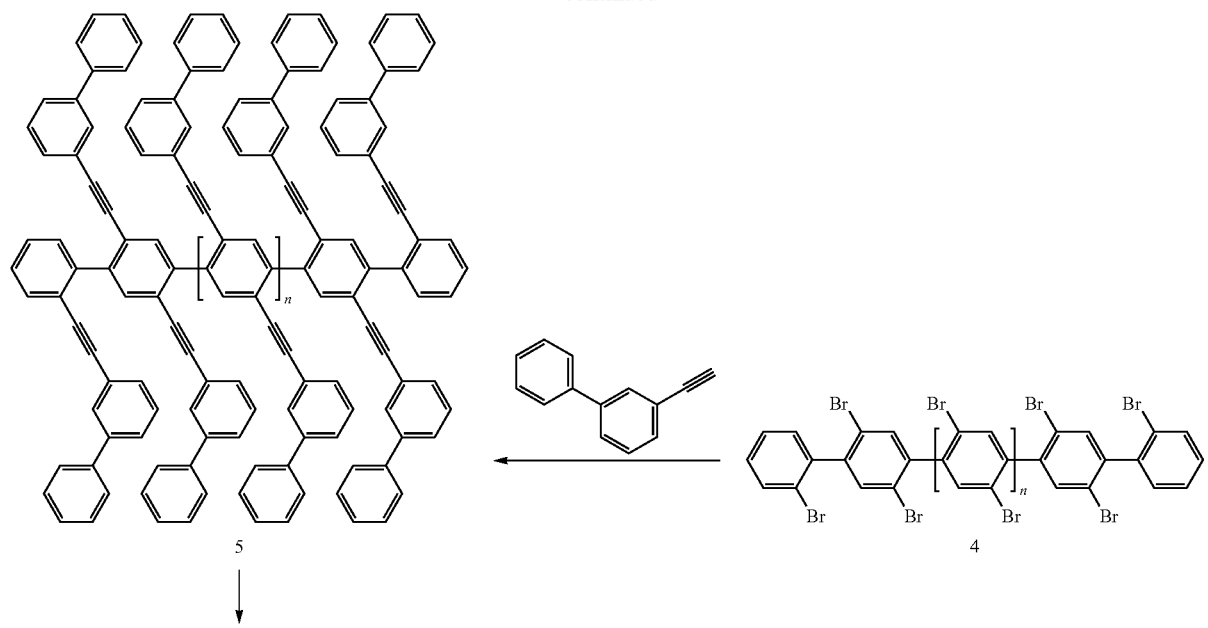
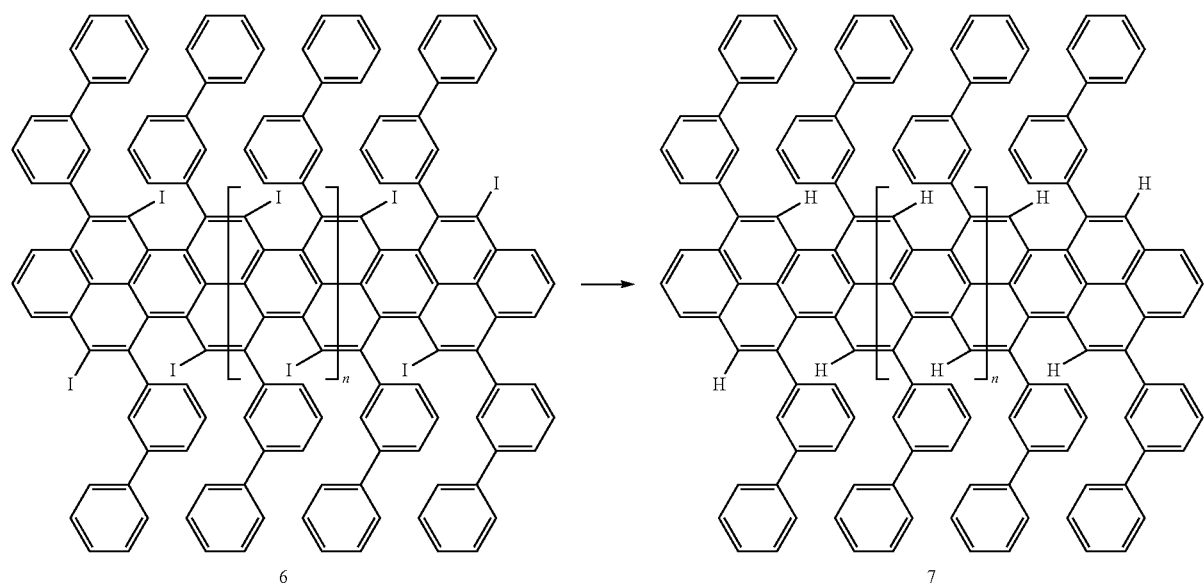

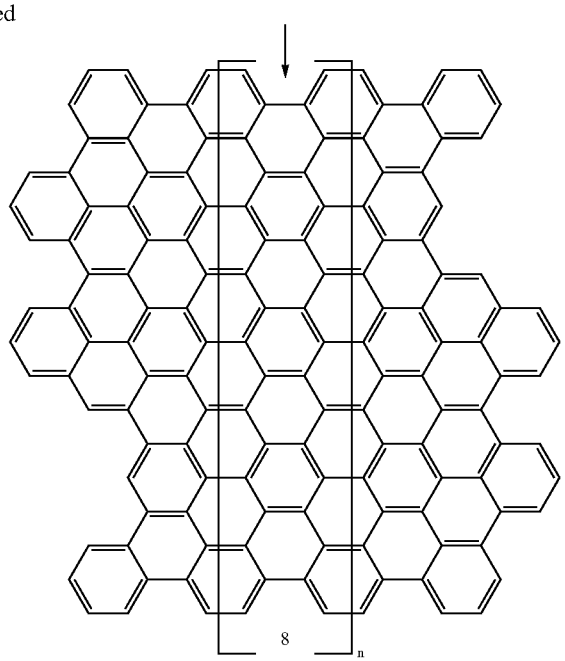

As shown in Reaction Scheme C, a mixture of 1 equivalent 2,5-dibromobenzene-1,4,-diboronate (1), 1.02 equivalents 2,5-dibromo-1,4-diiodobenzene (2), 0.2 equivalents tetrakistriphenylphosphine palladium, dimethoxyethane, and 2M aqueous sodium carbonate solution (6 equivalents) is heated at 70° C. for 8 hours. To this reaction mixture containing intermediate 3 is added 0.05 equivalents 2-bromophenylboronic acid pinacol ester is added and the mixture is heated at 70° C. for 8 hours. After filtering, the filtrate is concentrated under reduced pressure and the residue is washed with water and then with methanol to yield crude intermediate 4 wherein n is an integer of 1 to 100,000. A mixture of 1 monomer equivalent intermediate 4, triethylamine as solvent, 0.05 equivalents tetrakistriphenylphosphine palladium, 2 equivalents copper (I) iodide, and 5 equivalents 3-ethynyl-1,1'-biphenyl is heated at 80° C. for 16 hours. The mixture is filtered and the filtrate is concentrated under reduced pressure. The residue is washed with methanol and then with heptane to provide crude intermediate 5. A solution of 2.2 equivalents iodine monochloride is added slowly to a solution of 1 monomer equivalent intermediate 5 in dichloromethane cooled at −78° C. After stirring at −78° C. for 1 hour, the mixture is treated with excess saturated aqueous sodium thiosulfate solution and then extracted with toluene. The extract is dried over magnesium sulfate and concentrated under reduced pressure to provide intermediate 6. A 2.5 M solution of n-butyl lithium in hexanes (2.2 equivalents) is added slowly to a solution of 1 monomer equivalent of 6 in tetrahydrofuran cooled at −78° C. After 5 minutes, excess methanol is added followed by dichloromethane. The mixture is washed with 5% aqueous hydrochloric acid solution, washed with water, and then dried over magnesium sulfate. Evaporation of solvents under reduced pressure yields intermediate 7. To a mixture of 1 monomer equivalent intermediate 7 and dichloromethane is added 50 equivalents of iron (III) chloride in nitromethane. After stirring for 20 hours at ambient temperature, the mixture is treated with methanol. The precipitate is filtered and washed in sequence with water, 5% hydrochloric acid solution, 25% ammonium hydroxide solution, water, methanol and pentane and then dried to under reduced pressure to yield graphene nanoribbon (8).

Example 4—Synthesis of Graphene Nanoribbon

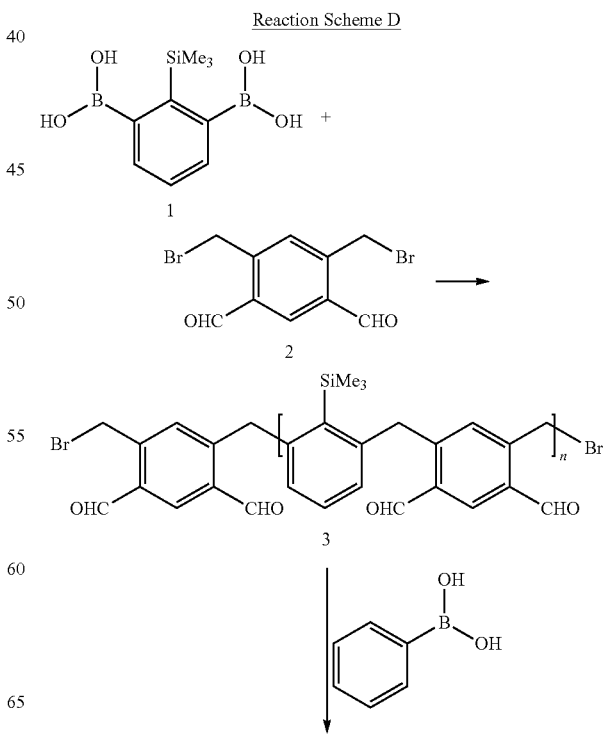

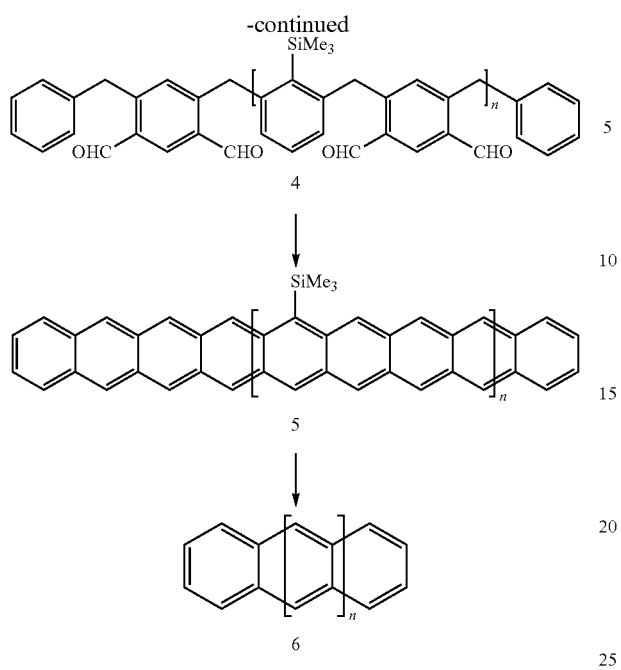

As shown in Reaction Scheme D, a mixture of 1 equivalent 2-trimethylsilyl-1,3-diboronic acid (1), 1.02 equivalents 4,6-bis(bromomethyl)isophthalaldehyde (2), 1.1 equivalents tripotassium phosphate, 0.002 equivalents dichloro(bis(1-(dicyclohexylphosphanyl)piperidine))palladium, and toluene is heated at 80° C. in air for 30 minutes. To this reaction mixture containing intermediate 3 is added 0.05 equivalents phenylboronic acid and the mixture is heated at 80° C. for 30 minutes. After cooling, water is added and the mixture is extracted with ethyl acetate. The extract is dried over magnesium sulfate and the solvents evaporated under reduced pressure to provide intermediate 4. A mixture of 1 monomer equivalent intermediate 4, 1 equivalent tosylamine, 0.3 equivalents boron trifluoride etherate and toluene is stirred at ambient temperature for 30 minutes. The mixture is filtered through a pad of silica gel and then the solvent is evaporated under reduced pressure to yield intermediate 5. To a solution of 0.5 monomer equivalent intermediate 5 in tetrahydrofuran is added 1 equivalent of a 1M solution of tetrabutylammonium fluoride in tetrahydrofuran. After stirring at ambient temperature for 12 hours, water and toluene are added and the organic layer is separated, washed with water, and dried over magnesium sulfate. Evaporation of the solvents under reduced pressure yields zigzag graphene nanoribbon 6.

Example 5—Use of a Graphene Nanoribbon in an Organic Thin Film Transistor

Organic thin film transistors can be made using the graphene nanoribbons of any one of examples 1 to 4 as an organic semiconductor layer. The organic thin film transistor is made up of a substrate; a gate electrode, a source electrode a drain electrode, an insulator layer and an organic semiconductor layer adjacent to the substrate; and a source-drain cover. The source drain cover is controllable by applying a voltage to the gate electrode whereby the organic thin film transistor performs and on-off operation. The source electrode and the drain electrode are formed on the substrate so that they are opposed to each other and the organic semiconductor layer is formed so as to cover the source electrode and the drain electrode. The insulating layer is formed so as to cover the semiconductor layer; and the gate electrode is formed above the insulating layer. The source electrode and drain electrode are opposed to each other with a predetermined interval to form a gap; and the organic semiconductor layer is formed so as to cover the gap.

Example 6—Use of an Organic Thin Film Transistor

The organic thin film transistor of Example 5 can be used in liquid crystal displays (LCDs). The organic thin film transistor can be embedded in to the display itself, reducing crosstalk between pixels and improving image stability.

Example 7—Use of an Organic Thin Film Transistor

The organic thin film transistor of Example 5 can be used in Active Matrix Organic light-emitting diode (AMOLED) screens.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

While various compositions, methods and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a", "an", or "the" limits any particular claim containing such introduced claim recitation to embodiments containing only one such recitation, even when the same claim includes the introductory phrases "one or more" or "at least one" and indefinite articles such as "a", "an", or "the" (e.g., "a" and/or "an" and/or "the" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 substituents refers to groups having 1, 2, or 3 substituents. Similarly, a group having 1-5 substituents refers to groups having 1, 2, 3, 4, or 5 substituents, and so forth.

What is claimed is:

1. A method for synthesizing a graphene nanoribbon, the method comprising:
    coupling a first aryl monomer and a second aryl monomer to provide a linearly conjugated aryl compound intermediate;
    endcapping the linearly conjugated aryl compound intermediate;
    coupling the linearly conjugated aryl compound intermediate with a mono-substituted acetylene compound to provide a linearly conjugated aryl compound having a formula (I):

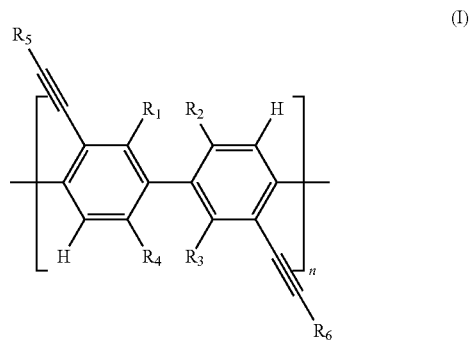

wherein n is an integer of 1 to 100,000;
    $R_1$ to $R_4$ are independently selected from H

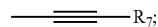

$R_5$ to $R_7$ are independently selected from H, alkyl, aryl, and trimethylsilyl;
    performing polycyclization of the linearly conjugated aryl compound to provide a graphene nanoribbon precursor, wherein performing polycyclization of the linearly conjugated aryl compound to provide a graphene nanoribbon precursor comprises heating to a temperature of about 20° C. to about 150° C. for about 1 to about 36 hours; and
    performing cyclodehydrogenation of the graphene nanoribbon precursor to provide the graphene nanoribbon.

2. A method for synthesizing a graphene nanoribbon, the method comprising:
    coupling a first aryl monomer and a second aryl monomer to provide a linearly conjugated aryl compound intermediate;
    coupling the linearly conjugated aryl compound intermediate with a mono-substituted acetylene compound to provide a linearly conjugated aryl compound having a formula (I):

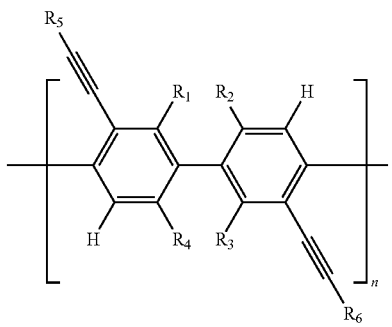

(I)

wherein n is an integer of 1 to 100,000;
$R_1$ to $R_4$ are independently selected from H and

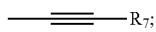—$R_7$;

$R_5$ to $R_7$ are independently selected from H, alkyl, aryl, and trimethylsilyl;
performing polycyclization of the linearly conjugated aryl compound to provide a graphene nanoribbon precursor; and
performing cyclodehydrogenation of the graphene nanoribbon precursor to provide the graphene nanoribbon.

3. The method of claim 2, wherein the first aryl monomer has a formula (II):

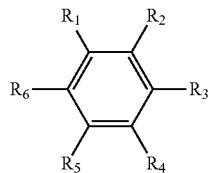

(II)

wherein $R_1$ to $R_6$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide; and
wherein the second aryl monomer has a formula (III):

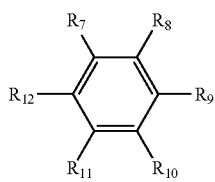

(III)

wherein $R_7$ to $R_{12}$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide.

4. The method of claim 2, wherein the first aryl monomer has a formula (V):

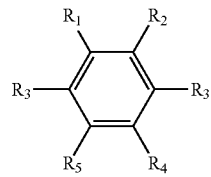

(V)

wherein $R_1$ to $R_5$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide; and
wherein the second aryl monomer has a formula (VI):

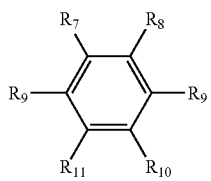

(VI)

wherein $R_7$ to $R_{11}$ are independently selected from hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, and a zinc halide.

5. The method of claim 2, wherein the first aryl monomer is a dihalophenyl diboronate compound and the second aryl monomer is a dihalodiodobenzene compound.

6. The method of claim 2, wherein coupling a first aryl monomer and a second aryl monomer to provide a linearly conjugated aryl compound intermediate comprises contacting the first aryl monomer with the second aryl monomer in a molar ratio of about 2:1 to about 1:2.

7. The method of claim 6, wherein coupling a first aryl monomer and a second aryl monomer to provide a linearly conjugated aryl compound intermediate further comprises adding a catalyst.

8. The method of claim 2, wherein coupling a first aryl monomer and a second aryl monomer to provide a linearly conjugated aryl compound intermediate further comprises adding a solvent, an aqueous base, or a combination thereof.

9. The method of claim 2, wherein coupling a first aryl monomer and a second aryl monomer to provide a linearly conjugated aryl compound intermediate further comprises heating to a temperature of about 20° C. to about 120° C. for a period of about 1 hour to about 36 hours.

10. The method of claim 2, further comprising coupling the linearly conjugated aryl compound intermediate with a mono-substituted acetylene compound to form the linearly conjugated aryl compound, wherein the mono-substituted acetylene compound has a formula (IV):

 (IV)

wherein $R_{12}$ is selected from hydrogen, aryl, polycyclic aryl, alkyl, copper, zinc, magnesium, tin, boron, silicon, indium, aluminum, lithium, sodium, zinc chloride, mercury chloride, manganese (II) chloride, magnesium bromide, tributyl boron lithium, tributyl aluminum lithium, dibutyl aluminum, trimethyl silicon, tributyl tin, or bis(cyclopentadienyl)dimethyl zirconium; and
$R_{13}$ is selected from hydrogen, trimethylsilyl, tert-butyldimethylsilyl, tert-butyldiphenylsilyl, triethylsilyl, triisopropylsilyl, alkyl, phenyl, furanyl, thiophenyl, pyridyl, or poly (m-phenylene) comprising about 2 to about 20 m-phenylene units.

11. The method of claim 10, wherein $R_{13}$ is hydrogen and $R_{14}$ is trimethylsilyl.

12. The method of claim 10, wherein coupling the linearly conjugated aryl compound intermediate with a mono-substituted acetylene compound to form the linearly conjugated aryl compound further comprises contacting the linearly conjugated aryl compound with a fluoride source.

13. The method of claim 12, further comprising adding a solvent.

14. The method of claim 1, wherein endcapping the linearly conjugated aryl compound intermediate occurs prior to the polycyclization of the linearly conjugated aryl compound to provide a graphene nanoribbon precursor.

15. The method of claim 1, wherein endcapping the linearly conjugated aryl compound intermediate comprises coupling the linearly conjugated aryl compound intermediate with an aryl monomer of formula (VI):

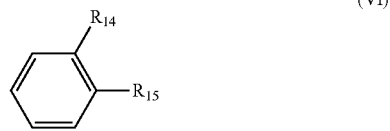 (VI)

wherein $R_{14}$ is hydrogen, fluorine, chlorine, bromine, iodine, lithium, trifluoromethanesulfonate, mesylate, or tosylate; and wherein $R_{15}$ is hydrogen, fluorine, chlorine, bromine, iodine, lithium, trifluoromethanesulfonate, mesylate, tosylate, bismuth, a boronic acid, a boronic ester, a boronate ester, an organoborane, an organotrifluoroborate, a magnesium halide, a stannane, a silicon trihalide, an organosilane, an acetyloxy, or a zinc halide.

16. The method of claim 15, wherein the unsubstituted ring carbons on the aryl monomer of formula VI, are independently substituted with groups selected from hydrogen, hydroxyl, a substituted or unsubstituted $(C_1-C_{20})$alkyl, $(C_1-C_{20})$hydroxyalkyl, $(C_1-C_{20})$alkoxy, $(C_1-C_{20})$alkylcarboxy, a substituted or unsubstituted aryl, $(C_1-C_{20})$haloalkyl, $(C_2-C_6)$alkenyl, $(C_2-C_6)$alkynyl, or an oxo.

17. The method of claim 1, wherein endcapping the linearly conjugated aryl compound intermediate comprises coupling the linearly conjugated aryl compound intermediate with a 2-bromophenyl boronate, a 2-chlorophenyl boronate, 2-bromo-1-iodobenzene, 2-chloro-1-iodobenzene, or a combination thereof.

18. The method of claim 1, wherein endcapping the linearly conjugated aryl compound intermediate comprises adding a palladium catalyst, a copper salt, an aqueous base, or a combination thereof.

19. The method of claim 1, wherein endcapping the linearly conjugated aryl compound intermediate comprises heating to a temperature of about 20° C. to about 150° C. for about 1 to about 36 hours.

20. The method of claim 1, wherein polycyclization of the linearly conjugated aryl compound to provide a graphene nanoribbon precursor comprises contacting the linearly conjugated aryl compound with a catalyst.

21. The method of claim 20, further comprising adding a solvent.

22. The method of claim 1, wherein performing the cyclodehydrogenation of the graphene nanoribbon precursor to provide the graphene nanoribbon comprises performing oxidative cyclodehydrogenation of the graphene nanoribbon precursor.

23. The method of claim 1, wherein performing the cyclodehydrogenation of the graphene nanoribbon precursor to provide the graphene nanoribbon comprises contacting the graphene nanoribbon precursor with iron (III) chloride.

24. The method of claim 23, further comprising adding at least one first solvent.

* * * * *

UNITED STATES PATENT AND TRADEMARK OFFICE
CERTIFICATE OF CORRECTION

PATENT NO. : 10,014,475 B2
APPLICATION NO. : 14/785323
DATED : July 3, 2018
INVENTOR(S) : Klein Page 1 of 1

It is certified that error appears in the above-identified patent and that said Letters Patent is hereby corrected as shown below:

In the Claims

In Column 32, Line 40, please delete "$R_1$ to $R_4$ are independently selected from H" and insert -- $R_1$ to $R_4$ are independently selected from H and -- therefor.

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*